(12) United States Patent
Kapsner et al.

(10) Patent No.: US 6,500,413 B1
(45) Date of Patent: Dec. 31, 2002

(54) HIGH PERFORMANCE COLOR-DEPOSITING SHAMPOO

(75) Inventors: Timothy Roland Kapsner, Minneapolis, MN (US); Peter Matravers, Plymouth, MN (US)

(73) Assignee: Aveda Corporation, Blaine, MN (US)

( * ) Notice: Subject to any disclaimer, the term of this patent is extended or adjusted under 35 U.S.C. 154(b) by 0 days.

(21) Appl. No.: 09/547,895

(22) Filed: Apr. 12, 2000

(51) Int. Cl.⁷ .............. A61K 7/06; A61K 7/00
(52) U.S. Cl. .......... 424/70.1; 424/401; 424/63; 424/70.6
(58) Field of Search ............... 424/401, 70.1, 424/70.6, 63

(56) References Cited

U.S. PATENT DOCUMENTS

| | | | |
|---|---|---|---|
| 4,797,481 A | 1/1989 | Garlisi et al. | 536/116 |
| 5,683,683 A | * 11/1997 | Scafidi | 424/70.19 |
| 5,741,769 A | 4/1998 | Erilli | 510/417 |

FOREIGN PATENT DOCUMENTS

| | | | |
|---|---|---|---|
| EP | 0559375 | 9/1993 | ............ A61K/7/08 |
| WO | WO 94/17783 | 8/1994 | ............ A61K/7/50 |

OTHER PUBLICATIONS

Pilot Chemical Company, Personal Care—Alkyl Glucoesters (Eucarol AGE's)—Techinal Bulletin.*

Wenninger, John A. and McEwen, Jr., G.N., International Cosmetic Ingredient Dictionary and Handbook ,1997, The Cosmetic, Toiletry, and Fragrance Association, Seventh Edition, vol. 2, 1673–1686.*

Chemistry and Technology of the Cosmetics and Toiletries Industry, Second Edition, Edited by D. F. Williams and W. H. Schmitt, Published by Blackie Academic & Professional, an imprint of Chapman & Hall, 2–6 Boundary Row, London SE1 8HN, UK., p. 21.

Pilot Chemical Company, Personal Care—Alkyl Glucoesters (Eucarol AGE's)—Technical Bulletin.

Technical Bulletin for Eucarol AGE's.

* cited by examiner

*Primary Examiner*—Jose' G. Dees
*Assistant Examiner*—Konata M George
(74) *Attorney, Agent, or Firm*—Karen A. Lowney, Esq.

(57) ABSTRACT

The present invention relates to cosmetic compositions, particularly foaming cleansing compositions, comprising a cationic component and an anionic alkyl glucoester surfactant. These compositions are particularly useful as color-depositing shampoos containing cationic dyes.

24 Claims, No Drawings

HIGH PERFORMANCE COLOR-DEPOSITING SHAMPOO

FIELD OF THE INVENTION

The invention relates to cosmetic compositions. More specifically, the invention relates to foaming cosmetic compositions.

BACKGROUND OF THE INVENTION

One of the most important characteristics of a hair cleansing composition is its ability to foam. Consumers perceive a high-foaming shampoo as being more effective, i.e., the greater the foam level, the greater the cleansing properties of the shampoo. To this end, most shampoos contain one or more primary surfactants, which have the dual effect of cleansing the hair as well as building a rich lather when applied to the hair. To a large extent, a majority of the primary surfactants used are high foam producing anionic surfactants, such as sodium lauryl sulfate, disodium laureth sulfosuccinate, and sodium methyl cocoyl taurate. Typically, these primary surfactants are combined with secondary surfactants, to build viscosity and enhance the foaming properties of the product. The usual secondary surfactants are either nonionic, such as lauraride DEA or amphoteric/zwitterionic, such as cocoamidopropyl betaine. Such systems are widely and very effectively used in a variety of hair-cleansing shampoos.

The aforementioned combination of primary and secondary surfactants does not prove useful, however, in hair care products containing a cationic component. Cationic components are highly favored in a variety of different types of skin care and hair care products: their cationic nature permits them to bind to the abundant anionic sites on both skin and hair, thereby giving them greater substantivity and staying power, and also other useful properties, such as antibacterial activity. Examples of widely used cationic cosmetic ingredients include cationic hair dyes, and quaternary ammonium compounds that are useful in hair styling and conditioning. However, this very property is the one which prevents them from being used in the typical surfactant system containing a strong anionic surfactant, in that cationic materials are not generally compatible with anionics. The combination of these two types of materials in a single product can result in the reduction of the foaming properties of the anionic surfactant, reduction of the amount of deposition of the cationic on the intended surface, or even the precipitation of the resulting anionic/cationic complex. Therefore, shampoos that must incorporate cationic components, such as coloring shampoos, have traditionally had to resort only to the use of amphoteric and nonionic surfactants, resulting in a product that produces very little foam, and a viscosity that is difficult to control without the use of additional gums or ethoxylated viscosifying agents. This problem does not arise when an anionic surfactant is combined with amphoteric and/or nonionic secondary surfactants, as viscosity can readily be built in such a system by the simple and inexpensive addition of sodium chloride. However, the added materials needed in the presence of cationics tend to inhibit foaming further, and to build a viscosity that is less aesthetically desirable than the viscosity that is built when adding sodium chloride to a traditional anionic surfactant system.

Several possible solutions have been proposed for permitting the combination of anionics with cationics, but most have their drawbacks. For example, the base can be made less anionic by the addition of high amounts of amphoteric or nonionic surfactants; however, this may result in unacceptable viscosity of the product. It has also been suggested to reduce the charge density on the cationic or anionic, usually by ethoxylation; however, any change in the structure of the original material runs the risk of altering the surfactant properties that made it desirable in the first place. Use of an excess of anionic can also be employed, and thereby any anionic/cationic complex formed can be solubilized in the excess; however, the use of large amounts of anionic can result in an alteration in the desired level of foam. The excess anionic may also greatly reduce, if not completely eliminate, the effectiveness of the cationic component.

For the foregoing reasons, it has been difficult to create a high performance hair color-depositing shampoo, since the cationic dyes so frequently used in hair coloring will not perform properly in the anionic surfactant system. This type of dye is particularly useful because of its ability to bind to the hair and its relative resistance to being washed off, but the formulation of a truly high quality color shampoo, having all the desirable qualities of a typical cleansing shampoo, by using the traditional type of shampoo system, has remained problematical.

SUMMARY OF THE INVENTION

The present invention provides a cosmetic composition suitable for application to the hair or skin comprising a cationic component, and at least one anionic surfactant which is a an alkyl glucoester. The compositions of the invention have excellent foaming properties, as well as viscosity, and permit effective deposit and retention of the desired cationic component on the skin or hair. In a preferred embodiment, the composition is a color-depositing shampoo containing at least one cationic dye.

DETAILED DESCRIPTION OF THE INVENTION

It has been unexpectedly discovered that it is now possible to formulate a composition having one or more cationic components in an anionic surfactant system, provided that the predominant anionic surfactant employed is an alkyl glucoester. The alkyl glucoesters useful in the present invention are disclosed in U.S. Pat. No. 4,797,481, the contents of which are incorporated herein by reference, and preferably have the formula:

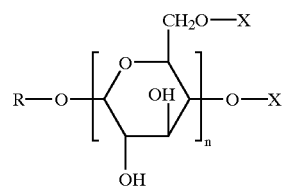

wherein R=a fatty alcohol radical, n=an integer <4, X is H, or

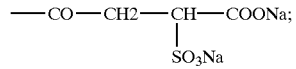

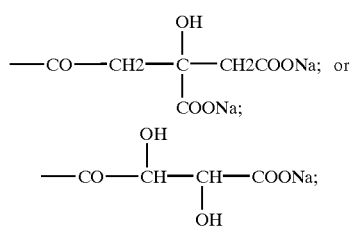

provided that at least one X is not H.

The fatty alcohol may be C6–C22 alcohols, and preferably is predominantly C12–C18 alcohols. These alkyl glucoesters are manufactured by Lamberti S.p.A, Albizzate, Italy, and are distributed in the US by Pilot Chemical Company(Santa Fe Springs, Calif.) under the trade name Eucarol AGE. Particularly preferred of the available AGEs are disodium cocopolyglucose sulfosuccinate(AGE-SS), disodium cocopolyglucose citrate(AGE-EC), and sodium cocopolyglucose tartrate(AGE-ET). These surfactants have been recommended for use in cleansing compositions, including shampoos, but only in the traditional combination with amphoteric/zwitterionic or nonionic secondary surfactants. It has now been surprisingly discovered, however, that these anionic surfactants, unlike other anionics, are compatible with a cationic component in the formulation, and can therefore be used in combination with a variety of cationic materials, which combination has either not previously been possible or which resulted in a very inferior product. In contrast to previous cationic-containing products, the composition containing the present combination retains an excellent foaming capacity, and can be routinely viscosified by the standard measures used in more traditional surfactant systems, i.e., by the interaction of the anionic with the secondary surfactant and salt. In a typical surfactant system, the alkyl glucoester is used in amount of about 1% to about 30%, preferably about 3% to about 15%, by weight of the total composition.

In a preferred embodiment, the alkyl glucoesters are combined with a cationic hair dye, to create a color-depositing shampoo with a performance superior to such shampoos currently available. Cationic dyes are widely used in hair coloring, and are commonly referred to as "basic" dyes, with a color and number identification, such as "Basic yellow 57" Such dyes are widely used, and a list can be found in the International Cosmetic Ingredient Dictionary and Handbook 8$^{th}$edition, 1999, the contents of which are incorporated herein by reference. An exemplary list includes, but is not limited to, Basic Brown 16, Basic Blue 99, Basic Red 76, and Basic Yellow 57. The amount of any given dye used in a formula will depend upon the color desired, but generally, in a color-depositing shampoo, the cationic dye(s) will constitute from about 0.01 to about 3%, preferably about 0.2% to about 1.5% by weight of the total composition.

Although the combination with cationic dyes is a particularly beneficial use of these alkyl glucoesters, it is also possible to obtain the benefit with other cationic materials commonly used in cosmetic compositions. For example, there are a number of very effective hair styling/conditioning agents that are cationic, for example, as stearalkonium chloride or cetrimonium bromide, that are commonly used in cream rinse formulations. However, they are generally incompatible with the predominant anionic surfactants of shampoos without major adjustments to the formula, and therefore have not been routinely used in conditioning shampoos. In the presence of an alkyl glucoester as the dominant anionic surfactant, hod this type can now be used in shampoos to impart a conditioning effect to a shampoo. Although less of an incompatibility is experienced between polymeric cationics and anionics, the alkyl glucoesters can also be beneficially combined with these cationic surfactants, for example, Polyquaternium-5, Polyquaternium-7, Polyquaternium-10, Polyquaternium-11, and Polyquaternium 24, or meadowfoam glyceryl quaternium. However, it is now possible to create a shampoo containing such styling components, using the alkyl glucoesters as the non-ionic surfactant, to achieve superior deposition and retention of the cationic styling agent on the hair with shampooing, in the same manner in which they are used in cream rinses and conditioners. Likewise, certain short chain quaternay ammonium salts, such as benzatkonium chloride, have a variety of useful properties, including antibacterial activity. Products such as these can now be used in an anionic surfactant-containing cleansing composition, providing the anionic surfactant is an alkyl glucoester.

In the cosmetic compositions of the invention, it will also in some cases be desirable to employ one or more secondary surfactants. As in traditional shampoos, it will be preferred that the composition contain an amphoteric/zwitterionic and/or nonionic surfactant, to complement the anionic alkyl glucoester, by stabilizing the foam and building the viscosity. Any surfactant of the secondary type can be used. Examples of useful amphoteric surfactants include, but are not limited to, alkyl betaines, alkylamido betaines, acylamphoglycinates, acylamphopropionates, and amine oxides or combinations thereof Examples of useful nonionic surfactants include, but are not limited to, ethoxylated fatty alcohols, N-alkylpyrrolidones, alkanolamides, and alkylpolyglucosides, or combinations thereof Each of these types of surfactants is used in substantially the same amounts as would be used in a traditional shampoo, i.e., at about 0.5 % to about 10% by weight of the total composition. It is also possible to incorporate a small quantity of an additional anionic surfactant, provided that the amount is not such as to interfere with the foaming and deposition properties of the composition. Ordinarily, the secondary anionic surfactant, if present, will be used in an amount of no more than 5%. Examples of anionic surfactants that can be used include, but are not limited to, alkyl sulfates, alkyl ether sulfates, isethionates, or phosphoric acid esters.

The compositions also can contain other cosmetic ingredients that are typically incorporated into cleansing or shampoo compositions. Examples of other types of cosmetic ingredients are conditioners, preservatives, opacifiers, colorants, frgance, and the like.

The invention will be further illustrated by the following non-limiting example.

EXAMPLES

EXAMPLE 1

A color-depositing shampoo of the present invention is prepared as follows:

| Material | Weight Percent |
| --- | --- |
| Purified water | QS |
| Disodium cocoamphodiacetate | 5.60 |
| Cocamidopropyl betaine | 7.50 |
| Cocamidopropyl amine oxide | 1.50 |
| Disodium cocopolyglucose citrate | 6.60 |
| PEG-120 methyl glucose dioleate | 0.50 |

EXAMPLE 1-continued

A color-depositing shampoo of the present invention is prepared as follows:

| Material | Weight Percent |
| --- | --- |
| Lauramide MEA | 2.50 |
| Dimethicone copolyol laurate | 0.50 |
| Basic brown 16 | 1.00 |
| Basic blue 99 | 0.25 |
| Basic Red 76 | 0.10 |
| Basic yellow 57 | 0.10 |

The basic dyes are added to a mixture of the four surfactants, and mixed well. The water and remaining ingredients are then added, and mixture is heated to 500° C. to dissolve all components. The mixture is cooled to room temperature, then the pH adjusted to between 5.0 and 6.5. If necessary, viscosity is adjusted by the addition of sodium chloride.

What we claim is:

1. A cosmetic composition for application to the hair or skin comprising a cationic component, and at least one anionic surfactant which is an alkyl glucoester, in which the cationic material is selected from the group consisting of a cationic dye and a non-polymeric quaternary ammonium salt.

2. The composition of claim 1 in which the alkyl glucoester has the formula:

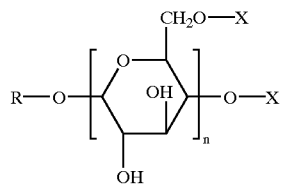

wherein R is a fatty alcohol residue, n is an integer <4, and X is H or

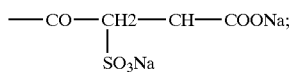

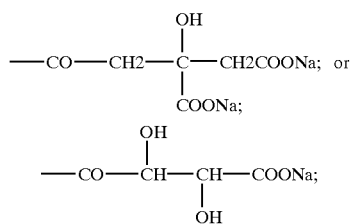

provided that at least one X is not H.

3. The composition of claim 2 in which the alkyl glucoester is selected from the group consisting of disodium cocopolyglucose sulfosuccinate, disodium cocopolyglucose citrate, sodium cocopolyglucose tartrate, and combinations thereof.

4. The composition of claim 3 in which the glucoester is disodium cocopolyglucose citrate or sodium cocopolyglucose tartrate.

5. A cosmetic composition for application to the hair or skin comprising a cationic component, and at least one anionic surfactant which is an alkyl glucoester, in which the cationic material is a cationic dye.

6. The composition of claim 1 which further comprises at least one surfactant selected from the group consisting of amphoteric surfactants and nonionic surfactants.

7. The composition of claim 6 which comprises both an amphoteric surfactant and a nonionic surfactant.

8. The composition of claim 1 which comprises a cationic dye, and at least one surfactant selected from the group consisting of an amphoteric surfactant and a nonionic surfactant.

9. The composition of claim 8 which is a color-depositing hair shampoo.

10. The composition of claim 1 which is a foaming cleansing composition.

11. The composition of claim 10 which is a conditioning shampoo.

12. The composition of claim 11 which comprises a cationic conditioning agent.

13. The composition of claim 11 which comprises a nonpolymeric cationic conditioning agent.

14. The composition of claim 1 which comprises from about 1 to about 30% alkyl glucoester.

15. A foaming cosmetic composition for application to the skin or hair comprising an alkyl glucoester having the formula:

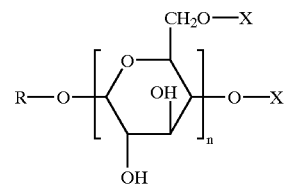

wherein R is a fatty alcohol residue, n is an integer <4, and X is H or

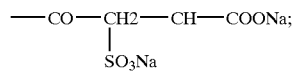

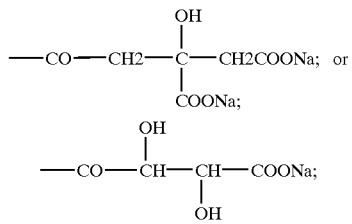

provided that at least one X is not H; combined with a cationic hair dye.

16. The composition of claim 15 in which the alkyl glucoester is selected from the group consisting of disodium cocopolyglucose sulfosuccinate, disodium cocopolyglucose citrate, and sodium cocopolyglucose tartrate.

17. The composition of claim 16 in which the alkyl glucoester is disodium cocopolyglucose citrate, or sodium cocopolyglucose tartrate.

18. The composition of claim 16 which comprises disodium cocopolyglucose citrate.

19. The composition of claim 15 which comprises from about 1 to about 30% of alkyl glucoester.

20. The composition of claim 15 which comprises from about 0.01 to about 3% of cationic dye.

21. The composition of claim 15 which further comprises at least one surfactant selected from the group consisting of an amphoteric surfactant and a nonionic surfactant.

22. The composition of claim 15 which comprises a cationic dye, disodium cocopolyglucose citrate or sodium cocopolyglucose tartrate, an amphoteric surfactant and a nonionic surfactant.

23. The composition of claim 15 which comprises from about 0.01 to about 3% cationic dye, from about 1 to about 30% disodium cocopolyglucose citrate or sodium cocopolyglucose tartrate, from about 0.5 to about 30% of an amphoteric surfactant, and from about 0.5 to about 30% nonionic surfactant.

24. The composition of claim 15 which comprises from about 0.2 to about 1.5% cationic dye, from about 3 to about 15% disodium cocoglucoside citrate, from about 0.5 to about 30% of an amphoteric surfactant, and from about 0.5 to about 30% nonionic surfactant.

* * * * *

UNITED STATES PATENT AND TRADEMARK OFFICE
CERTIFICATE OF CORRECTION

PATENT NO. : 6,500,413 B1
DATED : December 31, 2002
INVENTOR(S) : Kapsner et al.

It is certified that error appears in the above-identified patent and that said Letters Patent is hereby corrected as shown below:

Column 5,
Line 40, delete the following formula: 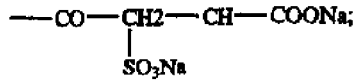

and insert the following formula: 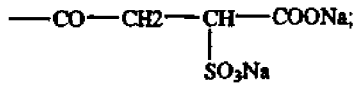

Signed and Sealed this

Ninth Day of November, 2004

JON W. DUDAS
*Director of the United States Patent and Trademark Office*